(12) United States Patent
Klun et al.

(10) Patent No.: US 7,081,545 B2
(45) Date of Patent: Jul. 25, 2006

(54) PROCESS FOR PREPARING FLUOROCHEMICAL MONOISOCYANATES

(75) Inventors: Thomas P. Klun, Lakeland, MN (US); Alan R. Kirk, Cottage Grove, MN (US); George G.I. Moore, Afton, MN (US); John C. Clark, White Bear Lake, MN (US); Zai-Ming Qiu, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 160 days.

(21) Appl. No.: 10/751,142

(22) Filed: Dec. 31, 2003

(65) Prior Publication Data

US 2005/0143595 A1 Jun. 30, 2005

(51) Int. Cl.
*C07C 269/02* (2006.01)
(52) U.S. Cl. .......................................... 560/27; 560/336
(58) Field of Classification Search ..................... None
See application file for complete search history.

(56) References Cited

U.S. PATENT DOCUMENTS

| | | | |
|---|---|---|---|
| 2,803,656 A | 8/1957 | Ahlbrecht et al. | |
| 3,776,805 A | 12/1973 | Hansen | |
| 4,321,404 A | 3/1982 | Williams et al. | |
| 4,540,497 A * | 9/1985 | Chang et al. | 428/375 |
| 4,566,981 A * | 1/1986 | Howells | 428/96 |
| 4,668,726 A * | 5/1987 | Howells | 524/225 |
| 4,778,915 A | 10/1988 | Lina et al. | |
| 4,920,190 A | 4/1990 | Lina et al. | |
| 5,144,056 A | 9/1992 | Lina et al. | |
| 5,446,118 A | 8/1995 | Shen et al. | |
| 5,462,797 A | 10/1995 | Williams et al. | |
| 5,578,657 A | 11/1996 | Inoue et al. | |
| 5,688,884 A | 11/1997 | Baker et al. | |
| 5,833,148 A | 11/1998 | Steinhilber et al. | |
| 5,955,512 A | 9/1999 | Numazawa et al. | |
| 5,959,775 A | 9/1999 | Joseph et al. | |
| 5,989,778 A | 11/1999 | Hozumi | |
| 6,017,603 A | 1/2000 | Tokuda et al. | |
| 6,180,200 B1 | 1/2001 | Ha et al. | |
| 6,664,354 B1 | 12/2003 | Savu et al. | |
| 2001/0005738 A1 | 6/2001 | Bruchmann et al. | |
| 2003/0192638 A1 | 10/2003 | Yang et al. | |

FOREIGN PATENT DOCUMENTS

| | | |
|---|---|---|
| EP | 1 142 912 A1 | 10/2001 |
| JP | 6-89462 A | 3/1994 |
| JP | 10-1659 A | 1/1998 |
| JP | 10-25453 A | 1/1998 |
| JP | 10-46109 A | 2/1998 |
| JP | 10-140090 A | 5/1998 |
| WO | 98/36325 A1 | 8/1998 |
| WO | 01/30873 A1 | 5/2001 |

* cited by examiner

*Primary Examiner*—Brian J. Davis
(74) *Attorney, Agent, or Firm*—Lisa P. Fulton

(57) ABSTRACT

A process for preparing fluorochemical monoisocyanates comprises reacting at least one fluorochemical alcohol represented by the formula $C_nF_{2n+1}SO_2NCH_3(CH_2)_mOH$, wherein n=2 to 5, and m=2 to 4, with 4,4'-diphenylmethane diisocyanate (MDI) in a solvent in which the resulting fluorochemical monoisocyanate is not soluble; wherein the molar ratio of fluorochemical alcohol:MDI is from about 1:1 to about 1:2.5.

16 Claims, No Drawings

PROCESS FOR PREPARING FLUOROCHEMICAL MONOISOCYANATES

FIELD

This invention relates to a process for selectively preparing fluorochemical monoisocyanates.

BACKGROUND

Various fluorinated acrylic resins containing urethane linkages are known to have water- and oil-repellency properties (see, for example, U.S. Pat. No. 4,321,404 (Williams et al.), U.S. Pat. No. 4,778,915 (Lina et al.), U.S. Pat. No. 4,920,190 (Lina et al.), U.S. Pat. No. 5,144,056 (Anton et al.), and U.S. Pat. No. 5,446,118 (Shen et al.)). These resins can be polymerized and applied as coatings to substrates such as, for example, textiles, carpets, wall coverings, leather, and the like to impart water- and oil repellency.

Typically, these resins comprise long chain pendant perfluorinated groups (for example, 8 carbon atoms or greater) because long chains readily align parallel to adjacent pendant groups attached to acrylic backbone units, and thus maximize water- and oil-repellency. However, long chain perfluorinated group-containing compounds such as, for example, perfluorooctyl containing compounds may bioaccumulate in living organisms (see, for example, U.S. Pat. No. 5,688,884 (Baker et al.)).

SUMMARY

In view of the foregoing, we recognize that there is a need for polymerizable water- and oil-repellent acrylic resins that are less bioaccumulative. Furthermore, in order for such compounds to be commercially attractive, we recognize that there is a need for an economical process for preparing starting compounds useful in their preparation.

Briefly, in one aspect, the present invention provides a process for preparing fluorochemical monoisocyanates that have short chain perfluorinated groups, which are thought to be less toxic and less bioaccumulative than longer chain perfluorinated groups (see, for example, WO 01/30873). These fluorochemical monoisocyanates can be reacted with acrylates, and then polymerized, to provide polymers having oil- and water-repellency properties.

The process of the invention comprises reacting at least one fluorochemical alcohol represented by the formula $C_nF_{2n+1}SO_2NCH_3(CH_2)_mOH$, wherein n=2 to 5, and m=2 to 4, with 4,4'-diphenylmethane diisocyanate (MDI) in a solvent in which the resulting fluorochemical monoisocyanate is not soluble; wherein the molar ratio of fluorochemical alcohol:MDI is from about 1:1 to about 1:2.5.

Surprisingly, it has been discovered that the process of the invention can be used to selectively prepare fluorochemical monoisocyanates in purities greater than 85% without any further purification. Furthermore, the process can be carried out using a substantially smaller excess of diisocyanate than other known processes (see, for example, U.S. Pat. No. 5,446,118 (Shen et al.), and U.S. Patent App. No. U.S. 2001/0005738 A1 (Bruchmann et al.)).

The process of the invention therefore meets the need in the art for an economical process for preparing starting compounds useful in the preparation of less bioaccumulative polymerizable water- and oil-repellent acrylic resins.

In another aspect, this invention also provides fluorochemical isocyanate compositions prepared by the process of the invention wherein said composition comprises greater than about 85% monoisocyanate.

DETAILED DESCRIPTION

Fluorochemical alcohols that are useful in carrying out the process of the invention include those represented by the following formula:

wherein n=2 to 5, and m=2 to 4 (preferably, n=2 to 4; more preferably, n=4).

Fluorochemical alcohols that are useful starting compounds include $C_2F_5SO_2NCH_3(CH_2)_2OH$, $C_2F_5SO_2NCH_3(CH_2)_3OH$, $C_2F_5SO_2NCH_3(CH_2)_4OH$, $C_3F_7SO_2NCH_3(CH_2)_2OH$, $C_3F_7SO_2NCH_3(CH_2)_3OH$, $C_3F_7SO_2NCH_3(CH_2)_4OH$, $C_4F_9SO_2NCH_3(CH_2)_2OH$, $C_4F_9SO_2NCH_3(CH_2)_3OH$, $C_4F_9SO_2NCH_3(CH_2)_4OH$, $C_5F_{11}SO_2NCH_3(CH_2)_2OH$, $C_5F_{11}SO_2NCH_3(CH_2)_3OH$, $C_5F_{11}SO_2NCH_3(CH_2)_4OH$, and mixtures thereof. Preferred fluorochemical alcohols include, for example, $C_2F_5SO_2NCH_3(CH_2)_2OH$, $C_4F_9SO_2NCH_3(CH_2)_2OH$, $C_4F_9SO_2NCH_3(CH_2)_4OH$, mixtures thereof. More preferred fluorochemical alcohols include, for example, $C_4F_9SO_2NCH_3(CH_2)_2OH$, $C_4F_9SO_2NCH_3(CH_2)_4OH$, and mixtures thereof. A most preferred fluorochemical alcohol is $C_4F_9SO_2NCH_3(CH_2)_2OH$.

Useful fluorochemical alcohols can be purchased from 3M (St Paul, Minn.), or can be prepared essentially as described in U.S. Pat. No. 2,803,656 (Ahlbrecht et al.) and U.S. Pat. No. 6,664,354 (Savu et al.).

The above-described fluorochemical alcohols can be reacted with 4,4'-diphenylmethane diisocyanate in a solvent to form the corresponding monoisocyanates. 4,4'-Diphenylmethane diisocyanate is commonly known as "methylene diisocyanate" or "MDI". In its pure form, MDI is commercially available as Isonate™ 125M from the Dow Chemical Company (Midland, Mich.), and as Mondur™ M from Bayer Polymers (Pittsburgh, Pa.).

The process of the invention can be carried out with a molar ratio of fluorochemical alcohol:MDI from about 1:1 to about 1:2.5. Preferably, the molar ratio of fluorochemical alcohol:MDI is from about 1:1 to about 1:2. More preferably, the molar ratio is from about 1:1.1 to about 1:1.5.

The process of the invention can be carried out in a solvent in which the resulting monoisocyanate is not soluble (that is, the solvent is one in which the monoisocyanate partitions out of so that it no longer participates in the reaction). Preferably, the solvent is a nonpolar solvent. More preferably, it is a nonpolar non-aromatic hydrocarbon or halogenated solvent.

Representative examples of useful solvents include cyclohexane, n-heptane, hexanes, n-hexane, pentane, n-decane, i-octane, octane, methyl nonafluoroisobutyl ether, methyl nonafluorobutyl ether, petroleum ether, and the like, and mixtures thereof. A mixture of methyl nonafluoroisobutyl ether and methyl nonafluorobutyl ether is available as HFE-7100 Novec™ Engineered Fluid from 3M (St. Paul, Minn.). Preferred solvents include, for example, methyl nonafluoroisobutyl ether, methyl nonafluorobutyl ether, petroleum ether, n-heptane, and the like.

Preferably, the solvent has a Hildebrand solubility parameter ($\delta$) of less than about 8.3 $(cal/cm^3)^{1/2}$ (about 17 $MPa^{1/2}$) and a hydrogen bonding index of less than about 4.

The Hildebrand solubility parameter is a numerical value that indicates the relative solvency behavior of a specific solvent. It is derived from the cohesive energy density (c) of the solvent, which in turn is derived from the heat of vaporization:

$$\delta = \sqrt{c} = \left[\frac{\Delta H - RT}{V_m}\right]^{1/2}$$

wherein:
ΔH=heat of vaporization,
R=gas constant,
T=temperature, and
$V_m$=molar volume For example, n-heptane has a Hildebrand solubility index of about 7.4 $(cal/cm^3)^{1/2}$ (about 15 $MPa^{1/2}$), and water has a Hildebrand solubility index of about 23.4 $(cal/cm^3)^{1/2}$ (about 48 $MPa^{1/2}$) (*Principles of Polymer Systems*, $2^{nd}$ edition, McGraw-Hill Book Company, New York (1982)).

The hydrogen bonding index is a numerical value that indicates the strength of the hydrogen bonding that occurs in a solvent. Hydrogen bonding values range from −18 to +15. For example, n-heptane has a hydrogen bonding value of about 2.2, and water has a hydrogen bonding value of about 16.2 (*Principles of Polymer Systems*, $2^{nd}$ edition, McGraw-Hill Book Company, New York (1982)).

The reaction can be carried out by combining the fluorochemical alcohol and MDI in the solvent. Preferably, the fluorochemical alcohol is added MDI, which is in the solvent, over time. Optionally, the fluorochemical alcohol can first be dissolved in a solvent such as, for example, toluene, and then added to the MDI in solution. Preferably, the reaction mixture is agitated. The reaction can generally be carried out at a temperature between about 25° C. and about 70° C. (preferably, between about 25° C. and about 50° C.)

Optionally, the reaction can be carried out in the presence of a catalyst. Useful catalysts include bases (for example, tertiary amines, alkoxides, and carboxylates), metal salts and chelates, organometallic compounds, acids, and urethanes. Preferably, the catalyst is an organotin compound (for example, dibutyltin dilaurate (DBTDL)) or a tertiary amine (for example, diazobicyclo[2.2.2]octane (DABCO)), or a combination thereof. More preferably, the catalyst is DBTDL.

After the reaction is carried out, the reaction product can be filtered out and dried. The reaction product typically comprises greater than about 85% of the desired fluorochemical monoisocyanate (preferably, greater than about 90%; more preferably, greater than about 95%).

Fluorochemical monoisocyanates that can be prepared using the process of the invention can be represented by the following formula:

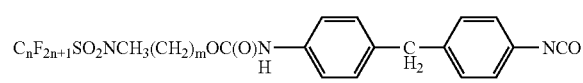

wherein n=2 to 5, and m=2 to 4.

Preferred fluorochemical monoisocyanates that can be prepared using the process of the invention include, for example:

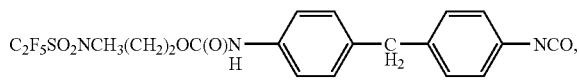

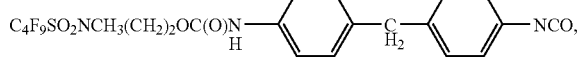

and

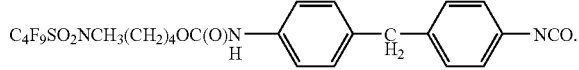

More preferred fluorochemical monoisocyanates prepared using the process of the invention include, for example:

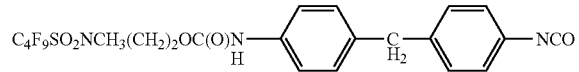

and

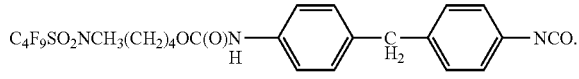

Fluorochemical monoisocyanates prepared using the process of the invention can be useful starting compounds in processes for preparing fluorinated acrylic polymers with water- and oil-repellency properties.

For example, fluorochemical monoisocyanates prepared using the process of the invention can be reacted with active hydrogen-containing compounds, materials, or surfaces bearing hydroxyl, primary or secondary amines, or thiol groups. The monomer produced by reacting a fluorochemical monoisocyanate prepared by the process of the invention with a hydroxy alkyl acrylate such as hydroxy ethyl acrylate, for example, can be polymerized (alone or with comonomers) to provide polymers that have useful water- and oil-repellency properties.

EXAMPLES

Objects and advantages of this invention are further illustrated by the following examples, but the particular materials and amounts thereof recited in these examples, as well as other conditions and details, should not be construed to unduly limit this invention.

| Designator | Glossary Name, Formula and/or Structure | Availability |
|---|---|---|
| BICMCH | 1,3 Bis-isocyanatomethyl cyclohexane | Sigma-Aldrich, Milwaukee, WI |
| DBTDL | Dibutyltin dilaurate | Sigma-Aldrich |
| Fluowet EA 600 | $C_6F_{13}CH_2CH_2OH$ | Clariant Corp. |
| HDI | 1,6-Diisocyanatohexane | Sigma-Aldrich |
| HFE-7100 | $C_4F_9OCH_3$ | 3M Company, St. Paul, MN |
| H12MDI | DESMODUR ™ W; 1,1'-Methylenebis-(4-isocyanatocyclohexane) | Bayer Polymers LLC, Pittsburgh, PA |
| MDI | MONDUR ™ M; 1,1'-Methylenebis-(4-isocyanatobenzene) | Bayer Polymers LLC |

-continued

Glossary

| Designator | Name, Formula and/or Structure | Availability |
| --- | --- | --- |
| MeFBSE | $C_4F_9SO_2N(CH_3)CH_2CH_2OH$ | 3M Company |
| MTBE | Methyl-t-butyl ether; $CH_3OC(CH_3)_3$ | Mallinckrodt Baker, Inc., Phillipsburg, NJ |
| Petroleum ether | | Mallinckrodt Baker, Inc. |
| PDI | 1,4-Phenylene diisocyanate | Sigma-Aldrich |
| TDI | Tolylene 2,4-disocyanate | Sigma-Aldrich |
| TMDI | Trimethyl-1,6-diisocyanatohexane | Bayer Polymers LLC |
| TMXDI | m-Tetramethylxylene diisocyanate | Cytec Industries, West Patterson, NJ |
| Toluene | $C_6H_5CH_3$ | Mallinckrodt Baker, Inc. |
| $C_4F_9SO_2N(CH_3)H$ | | 3M Company |
| $C_2F_5SO_2F$ | | 3M Company |
| $C_4F_9CH_2CH_2OH$ | | TCI America, Portland, OR |

Preparation of $C_4F_9SO_2N(CH_3)(CH_2)_4OH$

To a mixture of 64.8 g 25% $NaOCH_3$ in $CH_3OH$ (available from Aldrich), 100 ml $CH_3OH$, and 100 ml diglyme was added 93.9 g $C_4F_9SO_2NH(CH_3)$. The mixture was then stripped at 60° C./20 mTorr to 190.0 g. The stripped mixture was transferred to a paddle-stirred reaction flask using 125 mL diglyme, heated at 100° C. for 10 min (without a condenser) to remove traces of $CH_3OH$, and then treated with 75 g 4-chlorobutyl acetate (available from Aldrich). The resulting slurry was heated for 6 hr at 136° C., treated with 15 g of $CH_2Cl_2$, and heated for an additional 20 hr at 136° C. The resulting mixture was then washed with water, extracted with $CH_2Cl_2$, stripped to 237.8 g, and distilled (1-plate) to yield a 75.1 g main cut at 110–130° C./0.2–0.3 mTorr. The resulting material, $C_4F_9SO_2NCH_3C_4H_8$ acetate, was dissolved in 50 mL ethanol and treated with 5.0 g 50% NaOH diluted with 20 mL water with agitation. After 24 hr, infrared spectroscopy (IR) showed no acetate remaining. The product was extracted with $CH_2Cl_2$ to yield 65.7 g $C_4F_9SO_2NCH_3C_4H_8OH$, a pale tan liquid.

Preparation of $C_4F_9SO_2N(CH_3)(CH_2)_{11}OH$ $C_4F_9SO_2N(CH_3)(CH_2)_{11}OH$ was prepared using a procedure similar to that described above for preparing $C_4F_9SO_2N(CH_3)(CH_2)_4OH$. 175.9 g $C_4F_9SO_2NHCH_3$ and 121.4 g 25% $NaOCH_3$ were reacted to produce a solution of $C_4F_9SO_2NNaCH_3$ in about 100 mL diglyme. This solution was treated with 141 g 11-bromoundecanol (available from Aldrich) and heated at 100° C. for 20 hr to form a heavy precipitate. The reaction was quenched in about 600 mL warm water and the resulting lower layer was stripped at 50° C./0.5 mTorr to leave 269.9 g of $C_4F_9SO_2N(CH_3)(CH_2)_{11}OH$, a low-melting solid.

Preparation of $C_2F_5SO_2N(CH_3)CH_2CH_2OH$ $C_2F_5SO_2N(CH_3)CH_2CH_2OH$ can be prepared essentially as described in Example 1 Part A and Example 2 Part A of U.S. Pat. No. 6,664,354 (Savu et al.) with the exception that an equimolar amount of $C_2F_5SO_2F$ is substituted for $C_4F_9SO_2F$.

$C_2F_5SO_2N(CH_3)CH_2CH_2OH$ was prepared from $C_2F_5SO_2F$ by reaction with monomethylamine in MTBE, followed by stripping of the solvent, acidification with 19% sulfuric acid, then water washing and distillation at 5.5 mm at a head temperature of 69° C. to give $C_2F_5SO_2N(CH_3)H$. The $C_2F_5SO_2N(CH_3)H$ was then reacted with 3 equivalents of ethylene carbonate and 0.08 equivalents $K_2CO_3$ neat at 110° C. overnight. The product was isolated by successive washes with water, 3% sulfuric acid and water, followed by distillation at 0.5 mm at a head temperature of 98° C.

Example 1

Reaction of $C_4F_9SO_2N(CH_3)(CH_2)_4OH$ with MDI: 1.0:1.5

To a flask containing 37.5 g (0.15 mol) MDI in 75 g heptane (filtered at 50° C. through a C porosity frit), was added two drops of DBTDL at 50° C. and 38.5 g $C_4F_9SO_2N(CH_3)(CH_2)_4OH$ in 10 g heptane over 35 min. After reaction overnight at 50° C., the resulting solid was filtered, rinsed with heptane, and sucked dry under nitrogen to provide 69.67 g of a white powder that was 75.5% solids.

Example 2

Reaction of $C_2F_5SO_2N(CH_3)(CH_2)_2OH$ with MDI: 1.0:1.5

To a flask containing 37.5 g (0.15 mol) MDI in 75 g heptane (filtered at 50° C. through a C porosity frit), and two drops of DBTDL at 50° C. was added 25.7 g (0.10 mol) $C_2F_5SO_2N(CH_3)(CH_2)_2OH$ dropwise over 58 min. At 3.5 h, the resulting solid was filtered, rinsed with 120 g heptane, and sucked dry under nitrogen to provide 69.43 g of a white powder that was 71% solids, the remainder being heptane. (49.29 g yield, 97.2%).

Example 3

Reaction of MeFBSE with MDI: 1:1.1

To a 3 liter Morton flask was added 900 ml of dry heptane, followed by 283.4 g (1.1 mol) of fresh MDI. Stirring was begun as heat was applied. Added 4 drops of DBTDL. When the temperature of the solution reached 45° C., 357.2 g (1 mol) of MeFBSE was added in 5 portions, over a 1 hour period. Within 2 minutes, the product began separating as a finely divided, granular solid. The reaction was slightly exothermic (approximately 3 degrees Centigrade). When the addition of the MeFBSE was completed, the reaction was continued for another 1.5 hours at temperature. The reaction contents were then filtered under an atmosphere of nitrogen, and returned to the flask. An additional volume of heptane was added, and the solid was stirred for 15 minutes at 45° C., then filtered and rinsed with an additional volume of heptane under a nitrogen atmosphere. The resulting granular white solid was transferred to a large glass container, then flushed with nitrogen until the solvent was removed.

(Alternatively, the solid could have been vacuum dried at 45° C. until the solvent was removed.) Approximately 588 g of product was isolated (97% yield).

Example 4

Reaction of MeFBSE with MDI: 1:1.2

Example 4 was prepared by essentially following the procedure described for Example 3, with the exception that the molar ratio of MeFBSE:MDI was 1:1.2.

Example 5

Reaction of MeFBSE with MDI: 1:1.3

Example 5 was prepared by essentially following the procedure described for Example 3, with the exception that the molar ratio of MeFBSE:MDI was 1:1.3.

Example 6

Reaction of MeFBSE with MDI: 1:1.4

Example 6 was prepared by essentially following the procedure described for Example 3, with the exception that the molar ratio of MeFBSE:MDI was 1:1.4.

Example 7

Reaction of MeFBSE with MDI: 1:1.5

Example 7 was prepared by essentially following the procedure described for Example 3, with the exception that the molar ratio of MeFBSE:MDI was 1:1.5.

Example 8

Reaction of MeFBSE with MDI: 1:2

Example 8 was prepared by essentially following the procedure described for Example 3, with the exception that the molar ratio of MeFBSE:MDI was 1:2.

Example 9

Reaction of MeFBSE with MDI: 1.0:2.5

Example 9 was prepared by essentially following the procedure described for Example 3, with the exception that the molar ratio of MeFBSE:MDI was 1.0:2.5.

Example 10

Reaction of MeFBSE with MDI: 1:1.3 (Heptane/Toluene Solvent)

To a 1 liter, 3 necked, round bottomed flask equipped with a paddle stirrer, thermometer with temperature controller, and powder addition funnel, was added 45.6 g (0.18 mol) of MDI followed by 300 g of dry heptane, and 3 drops of DBTDL, under a nitrogen atmosphere. Stirring was begun and the temperature was raised to 45° C. To this clear solution was added, over 45–60 minutes, a solution of MeFBSE (150 ml toluene), which was azeotroped to remove traces of water. The MeFBSE solution was placed in a pressure equalized dropping funnel, and needed occasional heating to keep the MeFBSE in solution. As the reaction proceeded, a solid product precipitated. After the addition of the MeFBSE was completed, the reaction was continued at 45° C. for an additional 1.5 hours. It was filtered warm, rinsed with an equivalent volume of warm heptane, and then dried under an atmosphere of nitrogen.

Example 11

Reaction of MeFBSE with MDI: 1:1.3 (Petroleum Ether Solvent)

Example 11 was prepared essentially following the procedure described in Example 5, except substituting 400 ml of petroleum ether for the heptane. The product immediately precipitated as MeFBSE was added. The MeFBSE was added over a 1 hour period. The product was isolated after a 1.5 hour hold period, and rinsed once with warm petroleum ether, then dried with nitrogen. The yield was 82 g.

Example 12

Reaction of MeFBSE with MDI: 1:1.3 (HFE-7100 Solvent)

Example 12 was prepared essentially following the procedure described in Example 5, except substituting 300 ml of HFE-7100 for heptane. The MDI was not soluble to any large extent in this solvent. The product immediately precipitated. The product was rinsed with warm heptane of equal volume, and dried by nitrogen stream.

Comparative Example C-1

Reaction of $C_4F_9SO_2N(CH_3)(CH_2)_{11}OH$ with MDI: 1.0:1.5

A solution of 28.13 g (0.1125 mol) MDI in 65 g heptane at 50° C. was filtered into a 250 ml 3-necked round bottom flask and two drops of DBTDL were added to the flask. To this reaction mixture at 35° C. was added 4 roughly equal portions, 36.23 (0.075 mole) $C_4F_9SO_2N(CH_3)(CH_2)_{11}OH$ at t=0, 15, 30, and 45 min. After 3 h, the reaction was heated to 40° C. and the upper heptane phase was decanted from a solid product. Next, 65 g heptane was added and the reaction was heated to 70° C. After the solid became molten, the reaction was allowed to cool overnight to room temperature and the heptane layer was decanted off. Then, heptane (65 g) was added to the reaction, which was heated to 70° C. After stirring, the heptane layer was decanted off, leaving 52 g of a thick whitish solid.

Comparative Example C-2

Reaction of FLUOWET EA 600 with MDI: 1.5:1.0

A 3 neck 250 mL round bottom flask equipped with thermometer and overhead stirrer, was charged with 35.4 g (0.15 mole) MDI and 75 g heptane. The contents were heated to 50° C., and 2 drops of DBTDL were added. Next, 36.4 g (0.10 mol) FLUOWET EA 600 was added over 1 h via dropping funnel under nitrogen. Within 5 minutes a precipitate was evident. The reaction was run overnight, then diluted with 15 g heptane and vacuum filtered through filter paper under a stream of nitrogen. The filter cake was washed with 4 portions (totaling 50 g) of heptane at 50° C. The material was dried in a vacuum oven with a nitrogen bleed at 60° C. overnight to yield 53.66 g of a white powder.

Comparative Example C-3

Reaction of $C_4F_9CH_2CH_2OH$ with MDI: 1.0:1.5

In a manner essentially as described in Comparative Example C-2, 14.19 g (0.0568 mol) MDI in 30 g heptane was reacted with 10.0 g (0.0379 mol) of $C_4F_9CH_2CH_2OH$ to provide a solid that was filtered, but not dried.

Comparative Example C-4

Reaction of MDI with Trifluoroethanol, 1.5:1.0

To a 1 liter, 3 necked, round bottomed flask equipped with a paddle stirrer, thermometer with temperature controller, and pressure equalized liquid addition funnel, was added 125.3 g (0.50 mol) of MDI, followed by 400 g of dry heptane, and 3 drops of DBTDL, under a nitrogen atmosphere. Stirring was begun and the temperature was raised to 55° C. To this solution was added, portion-wise over 1 hour, 33.3 g (0.33 mol) of trifluoroethanol. A white solid immediately precipitated from the reaction, and the contents took on a thick, pasty consistency. The reaction was run overnight at 55° C. It was then filtered warm and rinsed with an additional volume of heptane, and vacuum dried at 45° C. overnight. About 100 g of a white solid was recovered.

Comparative Example C-5

Reaction of MeFBSE with MDI: 1:1.3 (MTBE solvent)

Comparative Example C-5 was prepared essentially following the procedure described in Example 5, except substituting 300 ml of MTBE for heptane. Much of the product does not precipitate in the MTBE. The solid was rinsed once with an equivalent volume of warm heptane.

Comparative Example C-6

Reaction of MDI with n-Octanol: 3.5:1

To a 1 liter, 3 necked, round bottomed flask equipped with a paddle stirrer, thermometer with temperature controller, and pressure equalized liquid addition funnel, was added 166.7 g (0.42 mol) of MDI followed by 400 g of dry heptane, and 3 drops of DBTDL, under a nitrogen atmosphere. Stirring was begun and the temperature was raised to 55° C. To this solution was added, portion-wise over 1 hour, 43.4 g (0.12 mol) of n-octanol. The reaction contents remained homogeneous, for the most part, at this temperature. The reaction was run overnight at 55° C. Upon cooling to room temperature, a white solid precipitated. The white solid was filtered, rinsed with room temperature heptane, pulled dry on the funnel under an atmosphere of nitrogen, and then dried overnight in a 45° C. vacuum oven. About 100 g of a white solid was recovered.

Comparative Example C-7

Reaction of MeFBSE with MDI: 1:1.3 (Toluene Solvent)

To a 1 liter, 3 necked, round bottomed flask equipped with a paddle stirrer, thermometer with temperature controller, and powder addition funnel, was added 45.6 g (0.18 mol) of MDI followed by 400 g of dry toluene, and 3 drops of DBTDL, under a nitrogen atmosphere. Stirring was begun and the temperature was raised to 45° C. To this clear solution was added, portion wise over 2 minutes, 50 g (0.14 mol) of MeFBSE. The contents were completely in solution. Shortly thereafter, a solid began to precipitate. Heating was continued for 1.5 hours more, then the reaction mixture was allowed to stir at room temperature overnight. Approximately 200 ml of heptane was warmed to around 50° C. and used to rinse the solid as it was filtered under an atmosphere of nitrogen. The white solid was pulled dry with the nitrogen stream, then transferred to a glass jar. Approximately 73 g of a white, free-flowing powder was recovered.

Comparative Example C-8

Reaction of $C_4F_9SO_2N(CH_3)CH_2CH_2OH$ with TMXDI: 1.0:1.5

In a manner essentially as described in Comparative Example C-13, 36.65 g (0.15 mol) TMXDI was reacted with 35.7 (0.1 mole) molten $C_4F_9SO_2N(CH_3)CH_2CH_2OH$. After reaction overnight, the solids were filtered and washed with heptane to provide 39.4 of a heptane wet solid.

Comparative Example C-9

Reaction of MeFBSE with TDI: 1.0:1.5

To a flask containing 26.2 g (0.15 mol) TDI, 65 g heptane, and two drops of DBTDL at 22° C., was added 35.7 g (0.10 mol) $C_4F_9SO_2N(CH_3)CH_2CH_2OH$ in four equal portions at t=0, 12, 24, and 36 min, with the temperature rising to 33° C. After 6 h of reaction the resulting solid was filtered, rinsed with heptane, and sucked dry under nitrogen to provide 60.98 g of a white free-flowing powder.

Comparative Example C-10

Reaction of MeFBSE with HDI: 1:2

To a 1 liter, 3 necked, round bottomed flask equipped with a paddle stirrer, thermometer with temperature controller, and powder addition funnel, was added 112 g (0.66 mol) of HDI followed by 350 g of dry heptane, and 3 drops of DBTDL, under a nitrogen atmosphere. Stirring was begun and the temperature was raised to 55° C. To this clear solution was added, portion-wise over 1.5 hours, 119 g (0.33 mol) of MeFBSE. Within 10 minutes of the beginning of MeFBSE addition, a white solid began precipitating from the reaction contents. The reaction was continued at 55° C. overnight. A larger volume of white solid formed, and was filtered under a nitrogen atmosphere, at room temperature. Residue in the flask was rinsed out with an additional 300 g of dry heptane. The recovered solid was dried in a vacuum oven at 45° C., using a drying tower of $CaCl_2$. This solid partially melted during the drying process. The yield was approximately 160 g.

Comparative Example C-11

Reaction of MeFBSE with TMDI: 1.0:1.5

To a 1 liter, 3 necked, round bottomed flask equipped with a paddle stirrer, thermometer with temperature controller, and powder addition funnel, was added 88.4 g (0.42 mol) of TMDI followed by 400 g of dry hexane, and 3 drops of DBTDL, under a nitrogen atmosphere. Stirring was begun and the temperature was raised to 55° C. To this clear solution was added, portion-wise over 2 hours, 100 g (0.28 mol) of MeFBSE. Most of the solid settled to the bottom of the flask, but as it reacted, the contents clarified. The reaction was continued at 55° C. for another hour, then kept at room temperature, overnight. A large volume of white solid was present. More hexane was added (about 100 g) to the contents of the flask, then it was chilled with an ice bath, and filtered under a stream of nitrogen. The solid appeared to be free-flowing, but upon vacuum drying overnight at 45° C., it coalesced to form a waxy solid.

Comparative Example C-12

Reaction of MeFBSE with PDI 1.0:1.5

To a 1 liter, 3 necked, round bottomed flask equipped with a paddle stirrer, thermometer with temperature controller, and powder addition funnel, was added 67.3 g (0.42 mol) of PDI followed by 400 g of dry heptane, and 3 drops of DBTDL, under a nitrogen atmosphere. The PDI had very little solubility in heptane. Stirring was begun and the temperature was raised to 55° C. To this slurry was added, portion-wise over 2 hours, 100 g (0.28 mol) of MeFBSE. Product formed almost immediately upon reaction with the MeFBSE. An additional 100 g of heptane was added, to aid in stirring. The reaction contents were filtered after an additional 2 hours of stirring at 55° C., and then rinsed with an equivalent volume of warm heptane. The resulting solid was transferred to an Erlenmeyer flask and heated with another volume of heptane, then filtered, under a nitrogen atmosphere. Additional heptane was used for rinsing. The solid was dried in a vacuum oven at 45° C. overnight. About 135 g of a light, powdery solid was recovered.

Comparative Example C-13

Reaction of $C_4F_9SO_2N(CH_3)CH_2CH_2OH$ with H12MDI: 1.0:1.5

In a manner essentially as described above, 39.3 g (0.15 mol) MDI was reacted with 0.10 mole of molten $C_4F_9SO_2N(CH_3)CH_2CH_2OH$ at about 90–100° C., which was delivered at a constant rate over 72 min from a dropping funnel wrapped with heating tape. After several hours, the reaction was allowed to cool to room temperature. The upper liquid phase was decanted off. The lower whitish phase was heated to 50° C., at which point it melted. It was then slurried with 50 g of heptane at 50° C. for 15 min, and the upper liquid phase was decanted off. Next, the solid was mixed at room temperature with heptane (60 g) and was vacuum filtered to yield 46.5 g of a free-flowing powder.

Comparative Example C-14

Reaction of MeFBSE with BICMCH: 1:1.5

To a 1 liter, 3 necked, round bottomed flask equipped with a paddle stirrer, thermometer with temperature controller, and powder addition funnel, was added 100.1 g (0.52 mol) of BICMCH, followed by 350 g of dry hexane, and 3 drops of DBTDL, under a nitrogen atmosphere. Stirring was begun and the temperature was raised to 55° C. To this clear solution was added, portion-wise over 1.5 hours, 122 g (0.341 mol) of MeFBSE. Within 10 minutes of the beginning of MeFBSE addition, an oil began separating from the reaction contents. The reaction was continued at room temperature, overnight. A waxy solid formed. The solvent layer was decanted and discarded. It was replaced with fresh hexane, and the mixture was heated to 55° C. with stirring. The solvent layer was decanted and discarded again. This was repeated an additional time, then the mixture was cooled to room temperature. The contents remained a waxy solid. The waxy solid was removed, then broken up into smaller pieces, and kept under a stream of nitrogen. The product had good solubility in acetone.

Sample Analysis:

All samples were prepared by weighing 20 to 25 mg of sample in a vial, immediately adding 100 μL of anhydrous methanol, and then 250 μL of anhydrous dimethyl sulfoxide (DMSO) to dissolve the sample. To this solution, 1 mL of MTBE containing a small amount of DBTL (2 drops in 10 mL MTBE) was added. The vial was heated at 50° C. for 20 minutes. The sample was cooled to room temperature, and the MTBE was removed by blowing a stream of nitrogen over the solution for 10 minutes. Two hundred and fifty μL of DMSO was added to the sample followed by 15 mL of acetonitrile. The sample solutions were each analyzed by high performance liquid chromatography (HPLC) under the following chromatographic conditions:

| | |
|---|---|
| Instrument: | Agilent 1100 HPLC |
| Column: | Merck Purospher RP18e, 5 μm, 125 × 3 mm |
| Solvent A: | Water |
| Solvent B: | Acetonitrile |
| Gradient: | 40% B to 100% B in 15 minutes and hold 100% B for 10 minutes |
| Flow Rate: | 0.5 mL/min |
| Injection: | 2 μL |
| Detector: | UV at 254 nm |

The methanolized samples were further analyzed by liquid chromatography-mass spectrometry (LC-MS) in positive electrospray ionization in order to identify the major components that were observed in the HPLC chromatograms.

Data is reported in Table 1 as UV Area (%) of the desired monoisocyanate product.

TABLE 1

UV Area (%) of Monoisocyanate

| Example | UV Area (%) | Example | UV Area (%) |
|---|---|---|---|
| 1 | 89.12 | C-1 | 20.12 |
| 2 | 85.89 | C-2 | 61.60 |
| 3 | 93.18 | C-3 | 78.53 |
| 4 | 95.34 | C-4 | 65.09 |
| 5 | 94.69 | C-5 | 14.69 |
| 6 | 94.23 | C-6 | 82.37 |
| 7 | 92.88 | C-7 | 70.95 |
| 8 | 94.22 | C-8 | 19.66 |
| 9 | 85.37 | C-9 | 83.98 |
| 10 | 93.94 | C-10 | 66.70 |
| 11 | 96.50 | C-11 | 15.31 |
| 12 | 90.04 | C-12 | 69.59 |
| | | C-13 | 54.14 |
| | | C-14 | 40.63 |

The referenced descriptions contained in the patents, patent documents, and publications cited herein are incorporated by reference in their entirety as if each were individually incorporated.

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

We claim:

1. A process for preparing fluorochemical monoisocyanates comprising reacting at least one fluorochemical alcohol represented by the formula $C_nF_{2n+1}SO_2NCH_3(CH_2)_mOH$, wherein n=2 to 5, and m=2 to 4, with 4,4'-diphenylmethane diisocyanate (MDI) in a solvent in which the resulting fluorochemical monoisocyanate is not soluble; wherein the molar ratio of fluorochemical alcohol:MDI is from about 1:1 to about 1:2.5.

2. The process of claim 1 wherein n=2 to 4.

3. The process of claim 2 wherein n=4.

4. The process of claim 2 wherein said fluorochemical alcohol is selected from the group consisting of $C_2F_5SO_2NCH_3(CH_2)_2OH$, $C_4F_9SO_2NCH_3(CH_2)_2OH$, $C_4F_9SO_2NCH_3(CH_2)_4OH$, mixtures thereof.

5. The process of claim 4 wherein said fluorochemical alcohol is selected from the group consisting of $C_4F_9SO_2NCH_3(CH_2)_2OH$, $C_4F_9SO_2NCH_3(CH_2)_4OH$, and mixtures thereof.

6. The process of claim 5 wherein said fluorochemical alcohol is $C_4F_9SO_2NCH_3(CH_2)_2OH$.

7. The process of claim 1 wherein said solvent is a nonpolar solvent.

8. The process of claim 7 wherein said solvent is a non-aromatic hydrocarbon or halogenated solvent.

9. The process of claim 1 wherein said solvent is selected from the group consisting of methyl nonafluoroisobutyl ether, methyl nonafluorobutyl ether, petroleum ether, n-heptane, and mixtures thereof.

10. The process of claim 1 wherein said solvent has a solubility parameter of less than about 8.3 $(cal/cm^3)^{1/2}$ and a hydrogen bonding index of less than about 4.

11. The process of claim 1 wherein said molar ratio of fluorochemical alcohol:MDI is from about 1:1 to about 1:2.

12. The process of claim 11 wherein said molar ratio of fluorochemical alcohol:MDI is from about 1:1.1 to about 1:1.5.

13. The process of claim 1 wherein said fluorochemical alcohol and said MDI are reacted in the presence of a catalyst.

14. The process of claim 13 wherein said catalyst is an organotin compound or a tertiary amine.

15. The process of claim 14 wherein said catalyst is dibutyltin dilaurate.

16. The process of claim 1 further comprising reacting the resulting fluorochemical monoisocyanate with a hydroxy alkyl acrylate.

* * * * *

UNITED STATES PATENT AND TRADEMARK OFFICE
CERTIFICATE OF CORRECTION

PATENT NO. : 7,081,545 B2
APPLICATION NO. : 10/751142
DATED : July 25, 2006
INVENTOR(S) : Thomas P. Klun It is certified that error appears in the above-identified patent and that said Letters Patent is hereby corrected as shown below:

Title Page,
Item (56), References Cited, U.S. PATENT DOCUMENTS, Line 12, delete "6,664,354" B1" and insert in place thereof -- 6,664,354, B2 --.

Column 2,
Line 22, delete "OH, mix" insert in place thereof -- OH, and mix --.
Line 29, delete "(St" and insert in place thereof -- (St. --.

Column 3,
Line 31, after "added" insert -- to --.
Line 38, after "C.)" insert -- . --.

Column 11,
Line 6, after "PDI" insert -- : --.

Column 13,
Line 15, before "mixtures" insert -- and --.

Signed and Sealed this

Fifteenth Day of April, 2008

JON W. DUDAS
*Director of the United States Patent and Trademark Office*